United States Patent [19]

Baldwin

[11] Patent Number: 5,584,288
[45] Date of Patent: Dec. 17, 1996

[54] MULTI-STAGE MOUTH-TO-MOUTH RESUSCITATOR VALVE

[76] Inventor: Gene R. Baldwin, 324 N. Gardiner Ave., Rockford, Ill. 61107

[21] Appl. No.: 191,788

[22] Filed: Feb. 3, 1994

[51] Int. Cl.⁶ .................................................. A61M 16/00
[52] U.S. Cl. .................. 128/202.28; 128/203.11; 128/205.24
[58] Field of Search ................ 128/202.28, 202.29, 128/203.11, 205.24

[56] References Cited

U.S. PATENT DOCUMENTS

| | | | |
|---|---|---|---|
| 3,099,985 | 8/1963 | Wilson et al. | 128/203.11 |
| 3,327,704 | 6/1967 | Bartlett, Jr. | 128/203.11 |
| 3,923,054 | 12/1975 | Bauer, Jr. | 128/203.11 |
| 4,811,730 | 3/1989 | Milano | 128/203.11 |
| 5,121,745 | 6/1992 | Israel | 128/203.11 |
| 5,146,914 | 9/1992 | Sturrock | 128/203.11 |
| 5,295,478 | 3/1994 | Baldwin | 128/203.11 |

Primary Examiner—Edgar S. Burr
Assistant Examiner—Aaron J. Lewis
Attorney, Agent, or Firm—Harold A. Williamson

[57] ABSTRACT

The invention is directed to a multi-stage mouth-to-mouth resuscitation valve in combination with a first valve to allow exhaled breath from a mouth of an operator to pass through the first valve to a mouth of a victim. The first valve is capable of assuming a position where exhaled breath of the victim can escape from the multi-stage resuscitation valve.

A second valve is provided to ensure that exhaled breath of a victim which may leak by the first valve does not reach the mouth of the operator. The second valve is positioned between the first valve and the mouth of operator.

7 Claims, 5 Drawing Sheets

MULTI-STAGE MOUTH-TO-MOUTH RESUSCITATOR VALVE

FIELD OF THE INVENTION

Mouth-to-mouth manually manipulated resuscitation devices of the type having a one-way valve through which air is delivered from an operator's mouth to a mouth and lungs of a victim.

BACKGROUND OF THE INVENTION

Resuscitation masks employed to co-operate with an operator's mouth and the face of a victim to be resuscitated have been in use for many years. Virtually all the masks in use today employ a one-way valve that is interposed between a mouth of an operator and a mouth of a victim who has stopped breathing and needs to be resuscitated to restore breathing.

In recent years there has been an increased awareness that a victim in need of resuscitation is possibly infected with the deadly acquired immune deficiency syndrome (AIDS) and considerable effort has been expended to prevent contamination of a rescuer or resuscitation mask operator. The virus responsible for AIDS is normally contained within a victim's body fluids. It is believed that absent blood in a victim's saliva, mucous or regurgitated matter there is little risk of cross contamination to the operator by breath exhaled by the victim.

Recently there has been a startling resurgence of tuberculosis in the world. This dreaded disease once believed to be wiped out is now experiencing a resurgence in populations of people living in urban and rural environments. In rural environments this disease is commonly carried by migrant farm workers.

Tuberculosis is an air-borne pathogen that is passed between infected individuals and healthy individuals via the exhaled breath from the lungs of a tuberculosis infected individual.

There have been many enhancements to the one-way valves employed in mouth-to-mouth resuscitation masks in order to prevent the transmission of the AIDS virus from a victim to an operator. Little, if anything, appears to have been done to specifically prevent air-borne pathogens present in a victim's exhaled breath from reaching an operator's mouth and lungs, with the exception of filters that restrict air flow.

One feature of the invention to be described herein after provides a remedy to this new concern regarding air-borne pathogens.

The level of technical sophistication in one-way valve structures for use in a resuscitation mask is shown in U.S. Pat. No. 4,811,730 ('730) issued Mar. 14, 1989 to A. J. J. Milano. The '730 patent teaches the use of a pair of one-way valves in a cardio pulmonary resuscitation (CPR) mask. One of the valves allows a rescuer's breath to pass into the nose and mouth of a victim while preventing the victim's exhaled breath from entering the rescuer's mouth. A second one-way valve member is provided to permit the rescuer's breath to pass therethrough and into an inflatable bladder while simultaneously preventing the air in the bladder from escaping. The inflatable bladder creates a resilient sealing means between a face of a victim and the resuscitation mask.

The first one-way valve member which is typical of the prior art includes a moveable valve member 42 which does not provide a hermetic seal with the walls of a chamber through which it travels. Air borne pathogens may leak past the moveable valve member and reach the rescuer's mouth and lungs. The instant invention prevent this type of cross contamination from occurring by providing a hermetic sealing between a moveable valve member of a one-way valve and the mouth and lungs of the rescuer.

In addition to public concerns regarding air-borne pathogens and one-way valves employed in, mouth-to-mouth resuscitation masks it is additionally recognized that many occupations such as, paramedics, firemen, hospital staff, lifeguards, etc., may require the personnel to administer CPR to a non-breathing victim who is removed from areas where more bulky equipment such as bag-valve-masks or demand valve resuscitators are stored. It has become a necessity to have these people carry a protective resuscitation device that can be applied to the victim immediately to start artificial ventilation while fellow workers bring bulkier equipment to the scene.

The device needs to be compact so it can be conveniently carried in a pocket by these personnel. The compactness should not compromise the efficiency of the device. Another criteria to consider is the elimination of as many steps as possible in the assembly of the device prior to resuscitation.

One of the more common type of devices in administering mouth-to-mouth ventilation is with an anesthia type mask. This type of mask seals around the victim's mouth and nose. These masks typically have a cuff or rim, the part of the mask that seals against the victim's face, that are made to hold entrapped air. This forms a flexible cushion which adjusts to seal various face sizes. This cuff is then connected to a dome that has a tubular fitting extending away from the dome for passage of air/gases into and out of the mask. A one-way valve or as it is frequently described, a nonrebreathing valve is inserted into this tube to allow the operator to blow into the mask and the victim's exhaled air exits away from the operator. This valve is necessary to help isolate the victim's breath from the operator.

To achieve the compactness needed for this type of mask it is taught by Laerdal, U.S. Pat. No. 4,062,357 ('357), that a dome part of the mask may be folded down to fit inside the walls of the cuff. The '357 patent shows a tubular stem at the apex of the dome extending upward inside a pocket that is formed when the dome is folded down into the cuff during storage. This tube is shown to be as long as the cuff is high. Adjacent to this tube is stored a small non-rebreathing valve, not shown in the patent.

The limited amount of room in this pocket, because of this tube, allows only for a valve of a small design to be stored on its side in this space. The smaller the valve the more restricted the air flow will be for both the victim's exhalation and inspiratory flow. Efficiency of air flow in a valve is so important that the ISO Draft International Standard #8382 sets maximum limits for the backpressure for both the patient's inspirator and exhalation air flow. A larger size valve in comparison to a valve of the same design but smaller will have less backpressure flow resistance. It is necessary to have the largest valve possible to meet those standards and to keep air flow backpressure to a minimum.

The smaller size valve also reduces the size of the mouthpiece on the valve. This small mouthpiece makes it more difficult for the operator to seal his lips around and at the same time blow into the valve in order to ventilate the victim's lungs.

The extending tubular stem also prevents the option of having the valve permanently attached to the mask. Any increase in height of the tube elevates the valve, should it be attached, and thus makes it more bulky.

To achieve maximum compactness when the mask is folded down while storing a larger valve that has more efficient air flow with a larger mouthpiece, the air inlet tube of the mask needs to be eliminated and the air inlet opening in the dome of the mask made larger enough to allow part of the valve housing to extend into this opening when the dome is folded down inside the walls of the cuff.

The multi-stage mouth-to-mouth resuscitation valve embodying the invention when employed in combination with a mask of a type to be described avoids the deficiencies noted with the use of prior art mask arrangements such as that shown in the Laerdal '357 patent.

SUMMARY OF THE INVENTION

The invention is directed to a multi-stage mouth-to-mouth resuscitation valve in combination with a first valve to allow exhaled breath from a mouth of an operator to pass through the first valve to a mouth of a victim. The first valve is capable of assuming a position where exhaled breath of the victim can escape from the multi-stage resuscitation valve.

A second valve is provided to ensure that exhaled breath of a victim which may leak by the first valve does not reach the mouth of the operator. The second valve is positioned between the first valve and the mouth of the operator.

It is therefore a primary object of this invention to provide a multi-stage mouth-to-mouth resuscitation valve that ensures that exhaled breath of a victim that may contain microscopic sized pathogens that may leak by a one-way valve in the multi-stage valve do not reach the mouth of an operator.

Another object of the invention is to provide a multi-stage mouth-to-mouth resuscitation valve that combines a pair of protective barriers to form a mask that allows an operator's fingers and hands that hold the mask to remove and reposition the mask under one of the protective barriers without the need to touch or position the operator's fingers on the side where the operator's mouth is placed. One of the barriers closest to the operator's face will also deflect the victim's breath away.

In the attainment of the foregoing objects the invention contemplates a multi-stage mouth-to-mouth resuscitation valve that includes in combination a moveable valve member that includes integral therewith a one-way valve to allow breath from a mouth of an operator to pass through the one-way valve of the moveable valve member to a mouth of a victim. The moveable valve member is capable of assuming a position where exhaled breath of the victim can escape from the multi-stage valve.

A sealing valve is also provided to ensure that exhaled breath of a victim which may leak by the moveable valve member does not reach the mouth of the operator. The sealing valve includes a one-way valve positioned between the moveable valve and the mouth of the operator.

In a preferred embodiment of the invention the resuscitation valve includes a first tubular extension, a second tubular extension and a chamber in communication with and securely interposed between the first and the second tubular extensions.

The moveable valve member is positioned in the chamber. The chamber has an opening to allow for passage of the exhaled breath of the victim. The chamber is additionally provided with a pressure release arrangement to allow venting of a region in the chamber between the moveable valve member and the sealing valve. The moveable valve member is moveable to a first position in response to the exhaled breath of the operator when the exhaled breath of the operator is delivered via the first tubular extension to the chamber and is prevented from escaping via the aforementioned opening. The moveable valve member is moveable to a second position when the exhaled breath of the operator ceases thereby allowing the exhaled breath of the victim to exit the chamber opening. The sealing valve may take the form of a one-way valve positioned in the first tubular extension.

In one embodiment of the invention the chamber includes a moveable valve member limit stop positioned in the chamber such that movement of the moveable valve member in the chamber at no time prevents passage through the pressure relief opening of either the exhaled breath of the operator and the exhaled breath of the victim that may leak by the moveable valve member.

In another embodiment of the invention a resuscitation mask is provided which includes in combination a multi-stage resuscitation valve, and a flexible barrier arrangement.

The resuscitation valve includes a first valve to allow exhaled breath from a mouth of an operator to pass through the first valve to a mouth of a victim. The first valve is capable of assuming a position where exhaled breath of the victim can escape from the multi-stage resuscitation valve. A second valve is provided to ensure that exhaled breath of a victim which may leak by the first valve does not reach the mouth of the operator. The second valve is positioned between the first valve and the mouth of the operator.

The flexible barrier arrangement is comprised of a first flexible barrier which is capable of providing a sealing contact with a face of the victim in a region adjacent to the nose/mouth of the victim. The first flexible barrier has an opening therethrough in which is secured a portion of the multi-stage resuscitation valve.

In addition to the first flexible barrier the flexible barrier arrangement of further includes a second flexible barrier which has an opening the periphery of which is integrally secured to the multi-stage mouth-to-mouth resuscitation valve to thereby provide a spatially separated region between the first and the second flexible barriers to thereby isolate the exhaled breath of the victim from the mouth and face of the operator and from the hand(s) of the operator that manually apply pressure on the first flexible barrier to position the first flexible barrier and the multi-stage resuscitation valve in the nose/mouth region of the victim.

BRIEF DESCRIPTION OF THE DRAWINGS

The description setforth above, as well as other objects, features and advantages of the present invention, will be more fully appreciated by referring to the detailed description and the drawings that follow. The description is of the presently preferred but, nonetheless, illustrative embodiments in accordance with the present invention, when taken in conjunction with the accompanying drawing wherein:

FIG. 13 is a partial cross-section of a prior-art resuscitation mask shown folded in upon itself to form a pocket in which a resuscitation valve is shown stored;

FIG. 14 is a partial cross-section of an embodiment of the invention which includes a mask and multi-stage valve stored therein;

FIGS. 15 and 16 illustrate cross-sections of an embodiment of multi-stage resuscitation valve in two operating conditions and having a configuration suitable for inclusion in the mask shown in FIG. 14;

FIG. 16 shows an embodiment of the invention having a multi-stage resuscitation valve in combination with a mask;

FIG. 17 is a partial section of the resuscitation mask which includes in combination a multi-stage resuscitation valve of the type shown in FIGS. 15 and 16, and FIGS. 18 and 19 illustrates another embodiment of the invention where the multi-stage resuscitation valves are shown in combination with a flexible barrier shield.

DETAILED DESCRIPTION OF THE PREFERRED EMBODIMENTS OF THE INVENTION

Reference is now made generally to FIGS. 1, 2, 3 and 4 which illustrate a variety of cross-sectional depictions of a prior art single stage one-way mouth-to-mouth resuscitation valve for use in a resuscitation mask.

Figures 1, 2, 3:
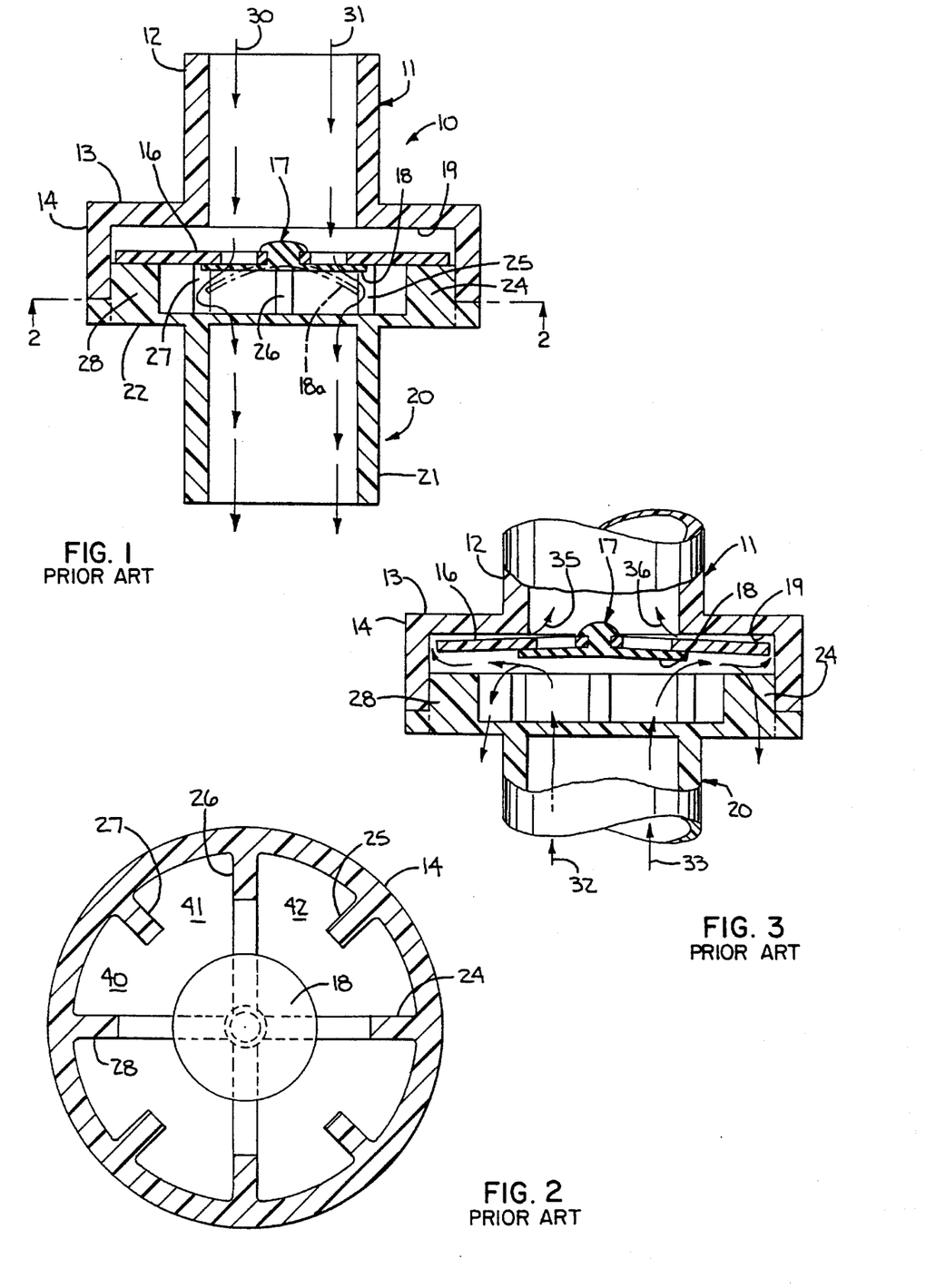
FIGS. 1, 2, 3 and 4 are a variety cross-sections of a prior art single-stage mouth-to-mouth resuscitation valve which embodies a problem overcome by the subject invention.
Figures 4, 5A, 5B:
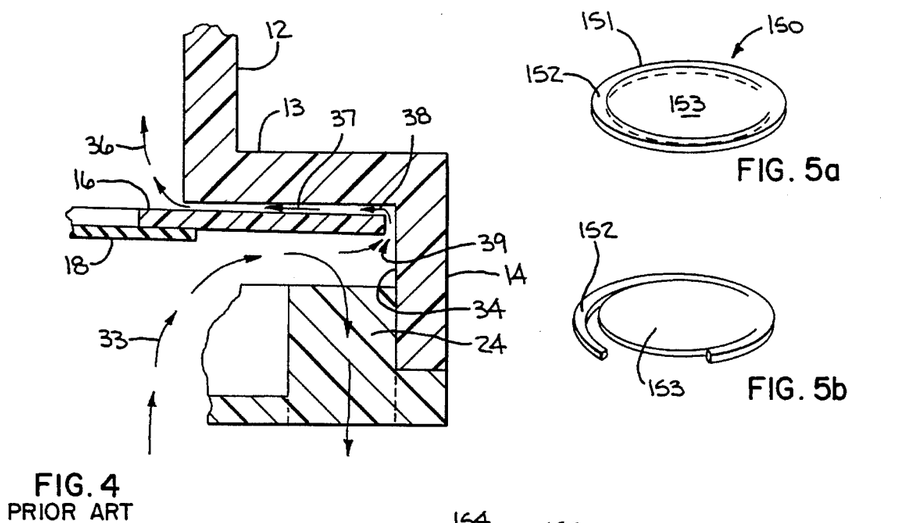
FIGS. 5, 5a, 5b, 5c, 6, 7 and 8 illustrate various sections of a multi-stage mouth-to-mouth resuscitation valve embodying the invention, as well as, operative details thereof in a number of operative conditions.

Particular attention is now directed to FIGS. 1 and 2 in which a one-way mouth-to-mouth resuscitation valve 10 is shown to include and upper housing 11 comprised of a tubular extension 12 having integrally formed therewith a radially disposed flange 13 and annular collar 14. A lower housing 20 is shown matingly positioned primarily within the annular collar 14 of the upper housing 11. The lower housing 20 includes a tubular extension 21 integrally formed with a lower housing flange 22 which has lower housing support ribs 24, 25, 26, 27 and 28 upon which a moveable circular valve member 16 rests when exhaled breath, as indicated by arrows 30, 31, of an operator not shown are delivered to and through tubular extension 12. The moveable valve member 16 has a centrally disposed one-way valve flap 18 which is shown in solid line in FIG. 1 to indicate that the flexible material of which it is composed is unflexed as is the case prior to an operator's breath having been delivered through the tubular extension 12 or as is shown in FIGS. 3 and 4 when a victim's exhaled breath is delivered via the lower housing 20 tubular extension 21.

The basic operation of this just described prior art one-way valve can best be understood by reference specifically to FIGS. 1, 2 and 3 where in FIG. 1 exhaled breath of an operator as indicated by arrows 30, 31 pass through the upper housing 11, tubular extension 12 and act upon the circular valve flap 18 of the one-way valve 17 integrally formed in moveable valve member 16. The exhaled breath of the operator causes the circular flap valve 18 to flex as is indicated broken line circular flap valve 18a as best seen in FIG. 1. The operator exhaled breath as generally indicated by arrows 30, 31 passes by and around the flexed circular flap valve 18a and through the lower housing 20 tubular extension 21 to a mouth of victim not shown. This operator exhaled breath fills the lungs of the victim in need of resuscitation.

The next step in the resuscitation process involves the expulsion of the operator's exhaled breath from the lungs of the victim through the lower housing 20 tubular extension 21. The exhaled breath of the victim is indicated generally by arrows 32 and 33. The exhaled breath of the victim acts upon the moveable valve member 16 and it's integrally associated one-way valve 17 to cause the moveable valve member 16 to move into an abutting position on a bottom surface 19 of radially disposed upper housing flange 13. This may be best seen in FIG. 3.

Movement of the moveable valve member 16 coupled with the victim's exhaled breath causes the circular flap valve 18 to seat firmly on an under surface 15 of the moveable valve member 16. This seating of circular valve flap 18 of the one-way valve 17 occurs simultaneously with the movement of moveable valve member 16 as just described. When the moveable valve member 16 is positioned as shown in FIG. 3 the victim's exhaled breath may escape as indicated by arrow extensions of the victim's exhaled breath arrows 32, 33, FIG. 3 via victim exhaled breath exhaust regions, three of which 40, 41 and 42 can be seen in FIG. 2.

The just described prior art one-way valve arrangement appears to meet the perceived need to prevent communication of regurgitated or exhaled victim body fluids from reaching a mouth and lungs of an operator via the upper housing 11 tubular extension 12.

Close examination this just described prior art one-way valve arrangement reveals that in order for the moveable valve member 16 to move freely without binding against an inner surface 34 of the upper housing annular flange 14 a radially disposed space as indicated by arrow 39 (see FIG. 3) must be provided at a radial periphery of the moveable valve member 16. The fit and finish of an upper surface, not referenced, of the moveable valve member 16 and the under surface 19 of the radially disposed flange 13 are such that an air tight seal is not established. While the degree of seal may be sufficient to block passage of a victim's exhaled body fluids and regurgitated matter, the seal provided between the moveable valve member is not sufficient to ensure that air borne pathogens such as tuberculosis do not make it past the moveable valve member 16 and into an operator's mouth. Ample evidence of exhaled breath of a victim moving past the moveable valve member 16 (see arrows 35, 36, FIG. 2 and arrows 37, 38, FIG. 4) can instantly be demonstrated by simply exhaling normally warm moist breath in the lower housing tubular extension 21 and watching the rapid condensation of this exhaled breath in the upper housing 11 tubular extension 12.

It is this exhaled victim's breath leakage through the prior art one-way valves that the now to be described invention overcomes.

Attention is now directed to the subject invention as depicted in FIGS. 5, 5a, 5b, 5c, 6, 7 and 8. These just noted figures should be studied in conjunction with the explanatory descriptive material that follows. As the description unfolds it will be appreciated that reference numeral employed with respect to the similar structural details in the preceding figures are related in that each reference numeral referencing a feature in the first four figures will have added to its' numerical value the numerical value of one hundred.

Figure 5:
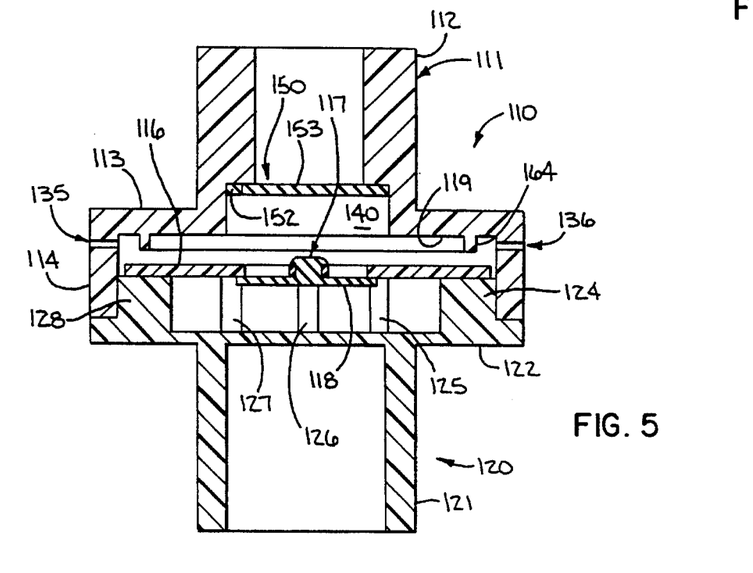

Specifically, attention is now directed to FIG. 5 where there is illustrated in full cross-section of a preferred embodiment of a multi-stage mouth-to-mouth resuscitation valve 110 that incorporates the invention. The one-way resuscitation valve 110 includes an upper housing 111 which includes tubular extension 112 through which exhaled breath of an operator will pass. The tubular extension 112 will provide a first opening in the housing capable of receiving exhaled breath from a mouth of an operator. The tubular extension 112 is provided integral therewith a radially disposed flange 113 and annular collar 114 as shown. The radially disposed flange 113 is provided on its' underside with a limit stop structure 164 the function of which will be described more fully hereafter.

The tubular extension 112 has positioned therein a sealing valve or sealing means as it may be termed from time-to-time hereinafter. The sealing valve 150 functions as a one-way valve to allow exhaled breath of an operator to pass freely thereby. FIGS. 5a and 5b depict three dimensionally the sealing valve 150 as a circular flapper valve 151 having a circular valve rim 152 and a flapper 153 shown flexed to allow passage of exhaled breath of the operator.

Figure 5C:
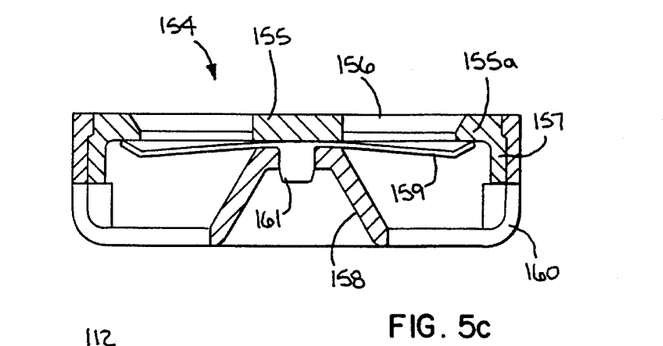

FIG. 5c illustrates another one-way valve 154 that may be substituted for the sealing valve 150 of FIG. 5. A full description of the one-way valve of FIG. 5c may be found in U.S. Pat. No. 5,127,397 issued Jul. 7, 1992 to O. B. Kohnke. Briefly the valve of FIG. 5c includes a housing provided by a valve seat 155 and a cover cap 158, as well as a circular valve flap 159. The valve seat 155 defines an outer wall 155a of the housing having inlet openings 156 and an annular flange 157. The cover cap 158 includes outlet openings, one of which 160 is referenced. The cover cap also includes a central protrusion 161 for centering and fixing the circular valve flap 159 which is constantly pressed against the valve seat 155.

Returning again to FIG. 5, a lower housing 120 includes a tubular extension 121 which provides a second opening in the housing that may be adapted to receive exhaled breath from a victim's nose/mouth. The lower housing tubular extension has integrally formed therewith a lower housing flange 122 that incorporates a moveable valve member support ribs 124, 125, 126, 127 and 128. A moveable valve member 116 is disposed as shown. Centrally disposed in the moveable valve member 116 is a one-way valve 117 that includes a circular flap valve 118. It will be recalled that in FIG. 2 described earlier that disposed between support ribs 24, 25, 26, 27 and 28 there were provided victim exhaled breath exhaust regions, three of which 40, 41, and 42 are referenced. The embodiment of the invention in FIGS. 5, 6, 7 and 8 include identical exhaust regions which may be thought of as providing a third housing opening.

The annular collar 114 of the upper housing is provided with an opening or openings 135, 136 which provide a pressure relief means such that exhaled breath of a victim that may leak by the moveable valve 116 may escape. More on this pressure relief function will follow.

The sealing means 150, a portion of upper housing tubular extension below the sealing means 150, the annular collar 114 and moveable valve member 116 create a chamber 140. The chamber 140 may be referred to in this specification and the appended claims as a "chamber means".

Figure 6:
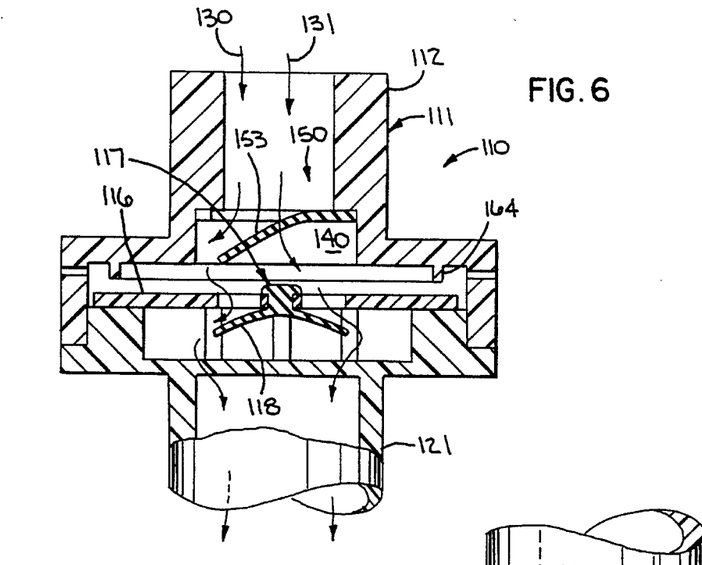

Turning now to FIG. 6 the multi-stage mouth-to-mouth resuscitation valve 110 is shown in a dynamic state where exhaled breath as indicated by exhaled breath arrows 130, 131 from an operator not shown passes through upper housing 111 tubular extension 112 and forces open flapper 153 of the sealing valve 150 and enters the chamber 140. The operator's exhaled breath then passes through the moveable valve member 116 and then passes flap valve 118 of the one-way valve 117 here shown deflected. The operator's exhaled breath thereafter exits the lower housing tubular extension 121 and into a mouth and lungs of a victim.

Figures 7, 8:
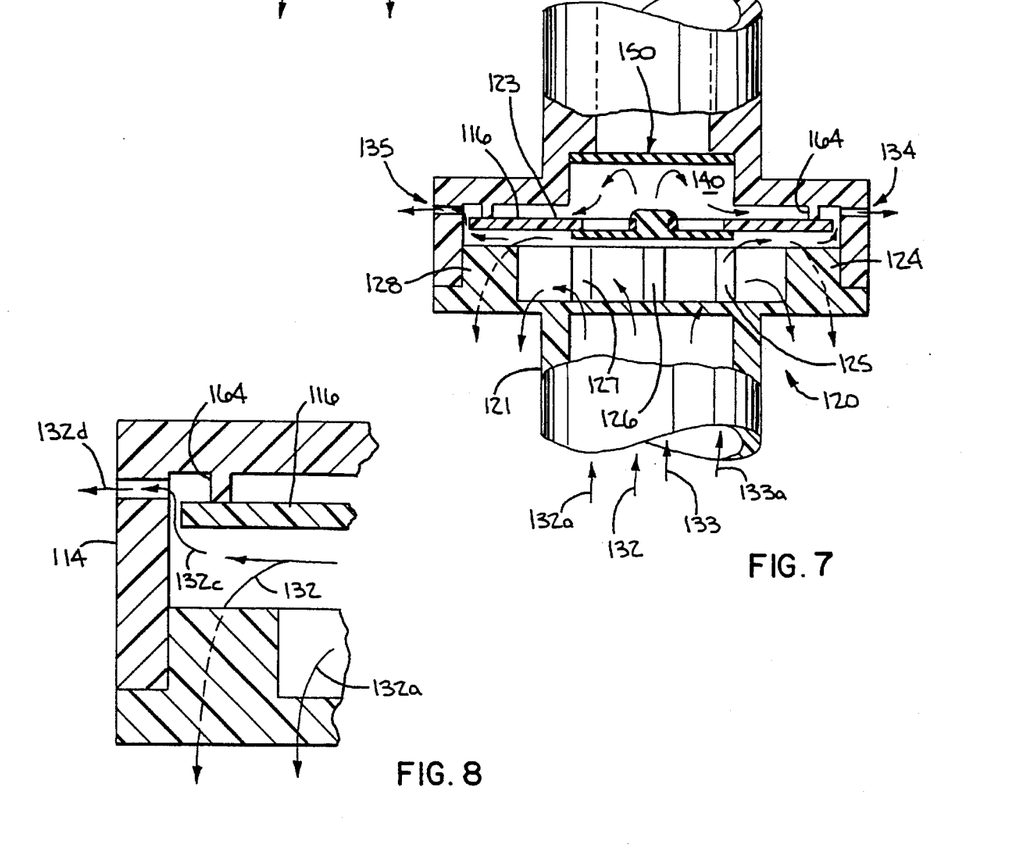

FIG. 7 illustrates the multi-stage mouth-to-mouth resuscitation valve 110 and its' internal valve components as the internal components become positioned during a period of time when exhaled breath of the victim is being delivered through the lower housing tubular extension 121. Four, victim exhaled breath arrows 132, 132a, 133 and 133a are shown passing upwardly through the tubular extension 121 forcing the moveable valve member 116 to move off of the moveable valve member support ribs of the lower housing 120. The moveable valve member is forced upward until an upper surface 123 thereof comes into abutting contact with the limit stop structure 164. The valve 150 by the nature of its design is biased to a positive closed position. Upward movement of the moveable valve member 116 coupled with leakage of the exhaled breath of a victim between the radial periphery of the moveable valve member 116 as indicated by arrows 132c and 132d (FIG. 8) are exhausted through the pressure relief opening 134.

Figures 9, 10, 11, 12:
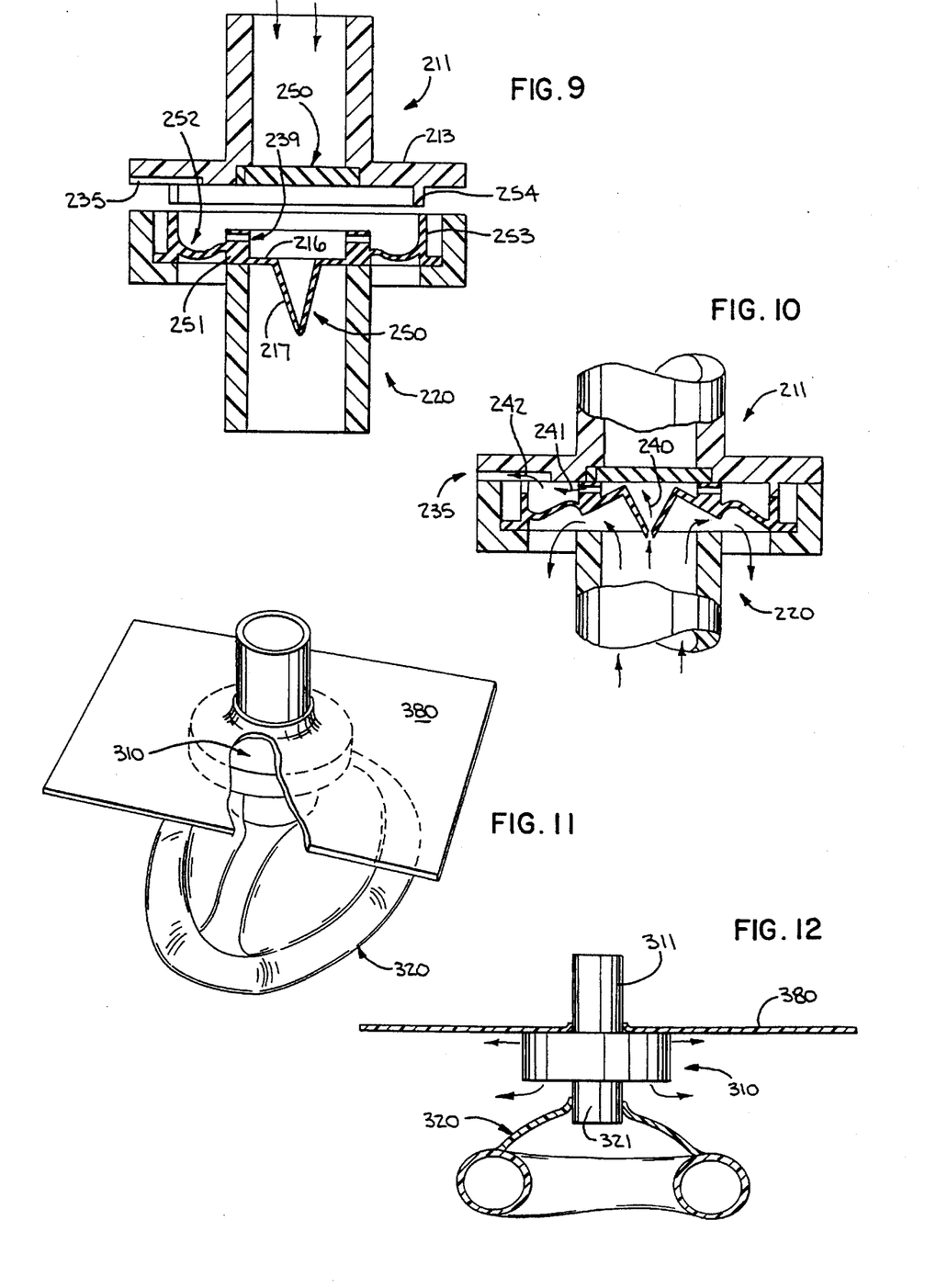
FIGS. 9 and 10 illustrate another embodiment of the invention in various sections where the operative details and conditions of a multi-stage mouth-to-mouth resuscitation valve embodiment are shown.
FIG. 11 illustrates in a three-dimensional drawing of another embodiment of the invention.
FIG. 12 is a partial section of FIG. 11 further showing details of this embodiment of the invention.

FIG. 9 and 10 illustrate yet another embodiment of the invention which employs a "duck bill" one-way valve 117 centrally disposed in a moveable valve member 216. The moveable valve member 216 includes four structural regions. The moveable valve member 216 is typically made of extremely resilient silicone or latex rubber. A central region 250 includes the "duck bill" one-way valve 217. A sealing ring 251, as shown, surrounds the central region 250 that includes the "duck bill" valve 217. FIG. 9 shows an upper housing 211 positioned above the lower housing 220 as the housings would appear prior to assembly. A bellows region 252 joins the sealing ring 251 to an annular resilient collar 253 as shown in the drawings. The "duck bill" one-way valve and its operation are well known in the art and therefore will not be described. A moveable valve member compression collar 254 integrally formed in an upper housing radial flange 213 is positioned as shown to ensure the compression of the annular resilient collar 253 when the upper housing 211 and the lower housing 220 are joined together as shown in FIG. 10.

The upper housing radial flange 213 also includes a pressure relief opening 235 that allows exhaled breath of a victim (see arrows 240, 241, 242 FIG. 10) that leaks through the duck bill valve 217 to ambient air surrounding the resuscitation valve 211.

It should readily be appreciated that this last described embodiment includes in combination a moveable valve member 216 that includes integrally therewith a one-way valve 217 that will allow exhaled breath from a mouth of an operator to pass through the one-way valve 217 to a mouth of a victim. The moveable valve member 216 is capable of assuming a position where the exhaled breath of a victim (see FIG. 10) can escape from the multi-stage resuscitation valve 211.

A sealing device 250 in the form of a one-way valve is provided to ensure that exhaled breath of a victim which may leak by the moveable valve member 216 does not reach the mouth of the operator.

FIG. 11 and 12 illustrate yet another embodiment of the novel multi-stage mouth-to-mouth resuscitation valve 310 in combination with a resuscitation mask 320 of conventional construction. The resuscitation mask 320 is designed to provide a sealing contact with a face of the victim (not shown) in a region adjacent to the nose/mouth of a victim. This sealing contact is enhanced by the fact that the mask 320 is a flexible barrier. In FIG. 12 it will be observed that tubular extension 321 is securely fitted in an upper portion of mask 320.

A second flexible barrier 380 is shown securely fitted around an upper housing tubular extension 311. This just described combination is highly advantageous in that the mask 320 and the flexible barrier 380 provide a spatially separated region between the mask 320 and the flexible barrier 380 to thereby isolate the mouth and face of the operator from the exhaled breath of the victim and the hand(s) of the operator that manually apply pressure on the mask 320 to position the mask and the multi-stage mouth-to-mouth resuscitation valve 310 in said nose/mouth region of a victim. The provision of a spatially separated region as herein described is also shown in my co-pending U.S. Pat. application titled: Double-Shield Mouth-To-Mouth Resuscitation Mask, Serial No. 08/181,837 filed Jan. 18, 1994.

Figures 13, 14, 15, 16, 17, 18, 19:
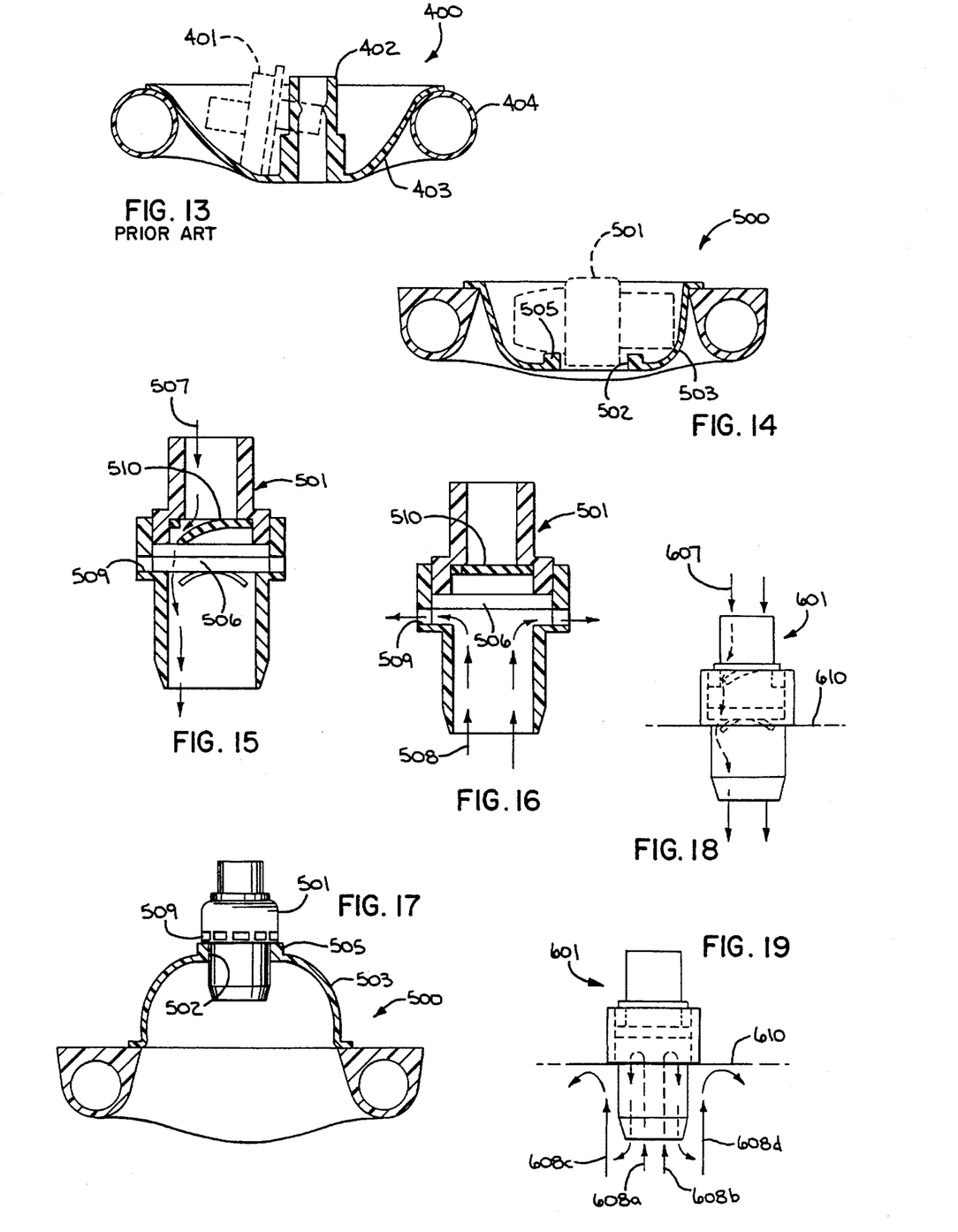

Reference is now made to FIG. 13 which illustrates in cross-section a resuscitation mask 400 of the type shown and described in Leardal U.S. Pat. No. 4,062,357. Shown in broken line in a stored position is a resuscitation valve 401 for use with the mask shown in section. An inlet tube 402 is shown centrally disposed and integrally connected to a dome 403 here shown inverted i.e. pushed down into flexible barrier or cuff 404. The flexible barrier or cuff 404 may also be referred to as a resilient deformable rim means. The common construction practice of the air inlet tube 402 in the dome 403 is to make the tube of a length sufficient to afford a tight fit on a valve stem or other connectors that may be used on this mask. This length of the air inlet tube 402 is necessary because the type of material used for the dome and tube stem, to achieve the folding affect of the dome, is a flexible polyvinylchloride (PVC) plastic. This type of plastic stretches and has poor memory. When a valve is inserted into an opening having peripheral walls made of PVC plastic and these walls make inadequate contact to a surface of the valve, there will be sufficient expansion of the plastic around the valve that will cause the valve to have a loose fit.

Reference is now made to FIG. 14 which is a partial cross-section of another embodiment of the invention which includes a resuscitation mask 500 and a multi-stage resuscitation valve 501 shown in broken line stored in a dome 503. The dome 503 is shown pushed down and inverted in FIG. 14, whereas in FIG. 17 the dome 503 is shown in a raised position as it would be when the mask 500 is in use. The dome 503 of the subject invention is made of a thermoplastic elastomer (TPE) such as polyurethane which provides an elastic memory sufficient to provide a valve with the need for only a small amount of surface contact. This permits an opening 502 to be constructed with a small raised rim or collar 505 or a thickening of a dome 503 wall section on the circumference of the opening, and yet insure that an inserted valve such as valve 501 will be secure and free from leakage.

It is advantageous to have the female opening of the mask a universal size, 22 mm. This opening also has to provide a firm fit to the standard size connectors. This allows the mask to be used with standard 22 mm male size connecters found in bag-valve-mask units and other ventilation equipment. When other equipment arrives the pocket mask can be fitted to the connectors of this equipment and thus eliminate the need to contaminate another mask. It is also advantageous to be able to remove the valve and replace it with another in the event the valve may get clogged with vomitus.

FIGS. 15 and 16 show in section another embodiment of multi-stage resuscitation valve that includes a first one-way valve 506 to allow exhaled breath (see arrow 507) from a mouth of an operator to pass through the first valve 506 to a mouth of a victim (not shown). The first valve 506 is capable of assuming a position (see FIG. 16) where exhaled breath (arrow 508) can escape from side openings such as 509. A second one-way valve 510 is provided to ensure that exhaled breath of a victim which may leak by the first valve 506 does not reach a mouth of the operator.

FIG. 17 shows a resuscitation mask 500 with a multi-stage resuscitation valve 501 positioned with a portion of the multi-stage i.e. nonrebreathing valve 501 partially extended in an opening 502 of the dome 503.

FIGS. 18 and 19 illustrate yet another embodiment of the invention where a multi-stage nonrebreathing resuscitation valve 610 is shown secured to a flexible barrier shield 610. The interior components of the valve 601 are the same as those shown and described with respect to the valve 501 of FIGS. 15 and 16. The sole difference residing in the removal of the side openings 509. The valve 601 as shown in FIG. 18 permits exhaled breath 607 from an operators mouth to pass through the valve 601 to the mouth of a victim not shown. FIG. 19 shows exhaled breath 608a, 608b, 608i and 608d from a victim's mouth (not shown) entering the valve 601 and coming back out as shown. Victim's exhaled breath arrows 608c and 608d are shown being deflected away from the flexible barrier shield 610.

It may be advantageous on some models of the mask, depending on the needs of the end user, to make the periphery of the opening with a wall thickness typical of the rest of the dome. This would allow maximum room for the multi-stage resuscitation valve to be permanently attached to the dome and the body of the valve would be nested inside a pocket formed when the dome is folded down inside the walls of the cuff. When the dome is fully extended, the unit is ready for immediate use without the need for any assembly.

There are several advantages of attaching the valve in the opening of the dome ready for use. This is advantageous in saving assembly time. It is also advantageous to prevent separation of the valve from the mask during assembly under difficult conditions such as poor lighting. It is also advantageous to reduce the risk of contamination to the valve where the operator places his mouth since it does not have to be touched by the operator's fingers when the dome is pushed upward into the working position.

Though the invention has been described with respect to a number of embodiments, many additional variations and modifications will immediately become apparent to those skilled in the art. It is therefore the intention that the appended claims be interpreted as broadly as possible in view of the prior art to include all such variations and modifications.

What I claim is new:

1. A multi-stage mouth-m-mouth resuscitation valve having a housing that has a first opening capable of receiving exhaled breath from a mouth of an operator and a second opening capable of receiving exhaled breath from a mouth of a victim, said resuscitation valve including in combination:

a moveable valve means in said housing, said moveable valve means having integral therewith a one-way valve to allow exhaled breath from an operator entering said first opening to move toward a victim through said one-way valve of said moveable valve means and said second opening,     said moveable valve means assuming a position during exhalation of breath of an operator's breath through said one-way valve, said moveable valve means assuming another position such that exhaled breath of a victim can escape from said multi-stage resuscitation valve housing, and a sealing valve means positioned in said housing between said moveable valve means and said first opening to ensure that exhaled breath of a victim which enters said second opening and leaks by said moveable valve means in said housing does not reach an operator.

2. The multi-stage mouth-to-mouth resuscitation valve of claim 1 wherein said resuscitation valve housing includes a first tubular extension, a second tubular extension and a chamber means in said housing in communication with and interposed between said first and said second tubular extensions.

3. The multi-stage mouth-to-mouth resuscitation valve of claim 2 wherein said moveable valve means is position in said chamber means, said chamber means in said housing having a third opening to allow for passage of exhaled breath of a victim and a pressure release means to allow venting of a region in said chamber means between said moveable valve means and said sealing valve means.

4. The multi-stage mouth-to-mouth resuscitation valve of claim 3 wherein said moveable valve means is moveable to said position in response to exhaled breath of an operator being delivered via said first tubular extension to said chamber means and is prevented from escaping via said third housing opening, and said moveable valve means is moveable to said other position when exhaled breath of operator ceases, thereby allowing exhaled breath of a victim to exit said third housing opening.

5. The multi-stage mouth-to-mouth resuscitation valve of claim 4 wherein said sealing valve means is a one-way valve positioned in said first tubular means.

6. A resuscitation mask including in combination a mouth-to-mouth multi-stage resuscitation valve, and a flexible barrier arrangement, said resuscitation valve having a housing that has a first opening capable of receiving exhaled breath an operator and a second opening capable of receiving exhaled breath from a victim, said resuscitation valve further including a moveable valve means and a sealing valve means in said housing, said moveable valve means having integral therewith a one-way valve to allow exhaled breath from an operator entering said first opening to move toward a victim through said one-way valve of said moveable valve means and said second opening, said moveable valve means assuming a position during exhalation of said breath by an operator through said one-way valve, said moveable valve means assuming another position such that exhaled breath from a victim can escape form said resuscitation valve housing, a sealing valve means positioned in said housing between said moveable valve means and said first opening to ensure that exhaled breath of a victim which enters said second opening and leaks by said moveable valve means in said housing does not reach an operator;

said flexible barrier arrangement having a first flexible barrier means capable of providing a sealing contact with a face of such a victim in a region adjacent to a nose/mouth of a victim, said first flexible barrier means having an opening therethrough in which is secured a portion of said multi-stage resuscitation valve housing.

7. The resuscitation mask of claim 6 wherein said flexible barrier arrangement further includes a second flexible barrier means having an opening the periphery of which is integrally secured to said multi-stage mouth-to-mouth resuscitation valve to thereby provide a spatially separated region between said first and said second flexible barriers to thereby isolate exhaled breath of a victim from an operator and from an operator's hands that manually apply pressure on said first flexible barrier to position said first flexible barrier and said multi-stage resuscitation valve in said, nose/mouth region of said victim.

\* \* \* \* \*